United States Patent [19]

Miyamoto

[11] Patent Number: 4,540,513
[45] Date of Patent: Sep. 10, 1985

[54] DECAPEPTIDE HAVING GONADOTROPIN RELEASING ACTIVITY

[75] Inventor: Kaoru Miyamoto, Shintou Arai, Japan

[73] Assignee: Kanegafuchi Kagaku Kogyo Kabushiki Kaisha, Osaka, Japan

[21] Appl. No.: 654,289

[22] Filed: Sep. 25, 1984

[51] Int. Cl.$^3$ .......................................... C07C 103/52
[52] U.S. Cl. ............................................ 260/112.5 R
[58] Field of Search .............................. 260/112.5 LH

[56] References Cited

U.S. PATENT DOCUMENTS 3,944,659 3/1976 Folkers et al. ........................ 424/95
4,005,063 1/1977 Gendrich et al. ......... 260/112.5 LH

OTHER PUBLICATIONS

Miyamoto et al., *Proc. Natl. Acad. Aci, USA,* vol. 18, pp. 3874–3878, Jun. 1984, Medical Sciences.

*Primary Examiner*—Delbert R. Phillips
*Assistant Examiner*—F. T. Moezie
*Attorney, Agent, or Firm*—Armstrong, Nikaido, Marmelstein & Kubovcik

[57] ABSTRACT

A decapeptide having the formula: pGlu-His-Trp-Ser-His-Gly-Trp-Tyr-Pro-Gly-NH$_2$. The decapeptide has an excellent gonadotropin releasing activity.

1 Claim, No Drawings

DECAPEPTIDE HAVING GONADOTROPIN RELEASING ACTIVITY

BACKGROUND OF THE INVENTION

The present invention relates to a novel decapeptide having gonadotropin releasing activity, i.e. corpus luteum hormon (LH) releasing activity and follicle stimulating hormon (FSH) releasing activity.

In 1971, a decapeptide having LH and FSH-releasing activity was isolated from hog hypothalamus and its chemical structure was determined as pGlu-His-Trp-Ser-Tyr-Gly-Leu-Arg-Pro-Gly-NH$_2$ hereinafter referred to as "LH-RH".

The present inventor has sought a naturally occuring unknown gonadotropin releasing factor whose structures is different from the above LH-RH. As a result of the seek, a novel peptide having gonadotropin releasing activity has been isolated from an extract of chicken hypothalamus and its chemical structure has been dertermined.

SUMMARY OF THE INVENTION

According to the present invention, there is provided a novel decapeptide having the formula:

pGlu-His-Trp-Ser-His-Gly-Trp-Tyr-Pro-Gly-NH$_2$.

The decapeptide has genadotropin releasing activity.

DETAILED DESCRIPTION

The decapeptide of the present invention having an excellent gonadotropin releasing activity is useful for treatment of hypogonadotropic hypogonadism.

The decapeptide of the present invention can be prepared, for instance, by extraction from hypothalamus of chicken or by chemical reaction.

The present invention is more specifically described and explained by means of the following Examples. It is to be understood that the present invention is not limited to the Examples and various changes and modifications may be made in the invention without departing the spirit and scope thereof.

EXAMPLE 1

Hypothalamus from 10,000 chickens was homogenized with Polytron after boilling the hypothalamus in 1N acetic acid, centrifuged at 10,000 r.p.m. for 1 hour to collect the supernatent. Approximate 40 l of the supernatent were obtained from about 10 kg of chicken hypothalamus. The supernatent was subjected to gel chromatography using Sephadex G-25 after desalting and concentrating by ultrafiltration.

When Sephadex G-25 column of 3 cm.×150 cm was used for the gel filtration, froctions having gonadotropin releasing acticvity were eluted to 870 ml to 1150 ml.

The fraction was further fractionated by ion-exchange high performance liquid chromatography with IEX 530 SIL (Toyo Soda Mfg. Co., Ltd.) having a 4×250 mm column. Elution was performed with a linear gradient series of 10 mM to 0.5 M ammonium formate containing 10% of acetonitril at PH 4.7.

Gonadotropin releasing activity was found in the fractions having an ionic strength of $\mu=0.08$ or $\mu=0.3$. The fraction eluted at an ionic strength of $\mu=0.08$ has been already determined as pGlu-His-Trp-Ser-Tyr-Gly-Leu-Gln-Pro-Gly-NH$_2$ by the present inventor.

The other active fraction eluted at an ionic strength of $\mu=0.3$ was purified finally by reversed phase high performance liquid chromatograpy. A 4×250 mm column of LS 410 (Toyo Soda Mfg. Co., Ltd.) was used and the elution was performed by linear gradient of 10% to 60% acetonitril. After the above reversed phase high performance liquid chromatography, about 7 μg of the purified decapeptide having gonadotropin releasing activity was obtained from about 10 kg of hypothalamus (10,000 chickens).

The activity of the purified was about 15×10$^8$ times more than that of the starting material.

The purified sample was hydrolyzed into amino acids with 6N HCl at 110° C. for 20 hours, and then subjected to determine the amino acid composition using an automatic amino acid analyzer (Hitachi 835, avairable from Hitachi Ltd.).

The purified sample was digested with chymotripsin or thermolysin for determination of amino acid sequence. The resulting peptide fragments were separated and isolated by reversed phase high performance liquid chromatography and respective peptide fragments were analysed for -N-termini by Dansyl method and for -C-termini by carboxylpeptidase method, to determine the structure of the sample. As a result, the structure of the sample was determined as the formula:

pGlu-His-Trp-Ser-His-Gly-Trp-Tyr-Pro-Gly-NH$_2$.

The decapeptide having the above strusture was synthesized according to a solid phase peptide synthesis method. The C-terminal amino acid derivative was coupled with benzhydrylamino-resin and then each amino acid derivative was sequentially bound to the peptide-resin from C-terminus. After Trp moiety was protected with N-formyl group, HF treatment was performed. The crude synthetic peptide was finally obtained by removing the N-formyl group by treating with 1% piperazine, and was purified by reversed phase high performance liquid chromatography to give a purified synthetic decapeptide.

The synthetic decapeptide was found to be identical to the natural one when they were compared each other by a chemical method using reversed phase high performance liquid chromatography and by a biological method using cultured rat hypophysis cells. The synthetic peptide and natural one were verified to be identical chromatographically on reverse phase HPLC. Furthermore, chymotryptic and thermolytic peptides from synthetic and natural preparations were identical on reverse phase HPLC. The gonadotropin-releasing potency of the synthetic and natural peptides were identical and were about 32% of that of mammalian LHRH and 8 times more potent than chicken LHRH as estimated from the bioassay with rat anterior pituitary cells.

EXAMPLE 2

The synthetic or natural decapeptides prepared in Example 1 was dissolved in 1N acetic acid so that the concentration was 1 μg/ml.

A series of half dilutions from 10.24 ng/ml to 10 pg/ml was prepared from the above solution.

Each sample solution in the series was dried in a rotary evaporator by evaporating 1N acetic acid.

The releasing activity was measured by monolayer culture method using rat prehypohysis cells. After rat prehypophysis cells were dispersed with tripsin and Viokase, the dispersed cells were washed well with a culture medium [Dulbecco's modified Eagle's medium (DMEM) containing 100 unit/ml gentamicin, 2.5 μ/ml fungizone, 5% horse serum, 5% human serum, and 2.5% fetal bovine serum]. The cells were inoculated at a density of $5 \times 10^4$ cells in each well of a plastic culture tray having 96 wells and precultured for 4 days.

Samples to be tested for gonadotropin releasing activity were added to the fifth-day culture and the culture was further incubated for 24 hours at 37° C. in the presence of 5% $CO_2$.

On the fifth day of the culture the above dried peptide sampls were dissolved in 0.5 ml of the Dulbecco's modified Eagle's medium (DMEM), 0.2 ml of aligot was aded to each well, and the cells were cultured in the well for additional 24 hours.

After the culture, the supernatent of the culture was withdrawn and assayed for LH and FSH with the radio imunoassay kit provided by NIH.

The results showed that the lowest detectable amount of both synthetic and natural ones was 160 pg/ml, and the specific activity was 3.1 ng/ml at the half maximum dose. Also, at the maximum dose, the LH releasing activity of the control was 200 ng/ml LH, while the activity of the decapeptide of the present invention was 3200 ng/ml LH, which is bigger than that of the control by about 3.5 times.

Those results show that the LH and FSH releasing activity values of the decapeptide of the present invention has 30% of the conventional LH-RH in specific activity.

What is claimed is:

1. A decapeptide having the formula:

pGlu-His-Trp-Ser-His-Gly-Trp-Tyr-Pro-Gly-$NH_2$.

* * * * *